(12) United States Patent
Ducharme

(10) Patent No.: US 8,486,093 B2
(45) Date of Patent: Jul. 16, 2013

(54) SYSTEMS AND METHODS FOR SECURING A GRAFT MEMBER TO TISSUE USING ONE OR MORE TACKING DEVICES

(75) Inventor: Richard W Ducharme, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 434 days.

(21) Appl. No.: 12/778,438

(22) Filed: May 12, 2010

(65) Prior Publication Data

US 2010/0292719 A1  Nov. 18, 2010

Related U.S. Application Data

(60) Provisional application No. 61/178,234, filed on May 14, 2009.

(51) Int. Cl.
*A61B 17/00* (2006.01)

(52) U.S. Cl.
USPC .......................... 606/151; 606/213

(58) Field of Classification Search
USPC ................ 606/151, 213, 232, 289, 295, 296, 606/302, 322, 219, 220; 623/23.72; 411/372.5, 411/373, 429, 431
See application file for complete search history.

(56) References Cited

U.S. PATENT DOCUMENTS

| | | | |
|---|---|---|---|
| 2,671,444 A | 3/1954 | Pease, Jr. | |
| 5,368,602 A | 11/1994 | De la Torre | |
| 5,695,525 A | 12/1997 | Mulhauser et al. | |
| 5,728,116 A | 3/1998 | Rosenman | |
| 5,759,570 A * | 6/1998 | Arnold | 424/443 |
| 5,766,246 A * | 6/1998 | Mulhauser et al. | 606/151 |
| 5,922,026 A | 7/1999 | Chin | |
| 6,425,900 B1 | 7/2002 | Knodel et al. | |
| 6,551,333 B2 | 4/2003 | Kuhns et al. | |
| 6,610,006 B1 * | 8/2003 | Amid et al. | 600/37 |
| 6,746,458 B1 | 6/2004 | Cloud | |
| 6,994,713 B2 | 2/2006 | Berg et al. | |
| 7,361,184 B2 * | 4/2008 | Joshi | 606/213 |
| 8,192,461 B2 * | 6/2012 | Kochman et al. | 606/216 |
| 2001/0029956 A1 * | 10/2001 | Argenta et al. | 128/897 |
| 2005/0171562 A1 | 8/2005 | Criscuolo et al. | |
| 2007/0299538 A1 * | 12/2007 | Roeber | 623/23.72 |
| 2008/0045978 A1 | 2/2008 | Kuhns et al. | |

FOREIGN PATENT DOCUMENTS

WO     WO 97/47244     12/1997

OTHER PUBLICATIONS

International Search Report and Written Opinion for PCT/US2010/034508 mailed Sep. 9, 2010, 15 pgs.
PCT Demand filed Mar. 14, 2011 for PCT/US2010/034508, 34 pgs.

* cited by examiner

*Primary Examiner* — Darwin Erezo
*Assistant Examiner* — Shaun L David
(74) *Attorney, Agent, or Firm* — Brinks Hofer Gilson & Lione

(57) ABSTRACT

The present embodiments provide systems and methods for repairing tissue using one or more tacking devices. In one embodiment, the system comprises a graft member and at least one protective member configured to enclose at least a portion of a tacking device. The protective member may include, without limitation, a pocket having an enclosure forming an interior space, a plug of material or a barrier layer. When at least one tacking device is deployed to couple the graft member to the tissue, at least a portion of the tacking device is enclosed by the protective member to reduce the exposure of the tacking device.

15 Claims, 6 Drawing Sheets

SYSTEMS AND METHODS FOR SECURING A GRAFT MEMBER TO TISSUE USING ONE OR MORE TACKING DEVICES

PRIORITY CLAIM

This invention claims the benefit of priority of U.S. Provisional Application Ser. No. 61/178,234, entitled "Systems and Methods for Securing A Graft Member to Tissue Using One or More Tacking Devices," filed May 14, 2009, the disclosure of which is hereby incorporated by reference in its entirety.

BACKGROUND

The present embodiments relate generally to medical devices, and more particularly, to apparatus and methods for securing a graft member to tissue.

Perforations in tissue or bodily walls may be formed intentionally or unintentionally. For example, an unintentional ventral abdominal hernia may be formed in the abdominal wall due to heavy lifting, coughing, strain imposed during a bowel movement or urination, fluid in the abdominal cavity, or other reasons. Intentional perforations may be formed, for example, during surgical procedures such as translumenal procedures. In a translumenal procedure, one or more instruments, such as an endoscope, may be inserted through a visceral wall, such as the stomach wall. During a translumenal procedure, a closure instrument may be used to close the perforation in the visceral wall. Depending on the structure comprising the perforation, it may be difficult to adequately close the perforation and prevent leakage of bodily fluids.

Attempts to seal perforations have been attempted by coupling a graft member to tissue. For example, during hernia repair, a graft material such as a mesh or patch may be disposed to cover the perforation. The graft material may completely overlap with the perforation, and the edges of the graft material may at least partially overlap with tissue surrounding the perforation. The graft material then may be secured to the surrounding tissue in an attempt to effectively cover and seal the perforation.

In order to secure the graft material to the surrounding tissue, sutures commonly are manually threaded through the full thickness of the surrounding tissue. In the case of a ventral abdominal hernia, the sutures may be threaded through the thickness of the abdominal wall, then tied down and knotted. However, such manual suturing techniques may be time consuming and/or difficult to perform.

Various tacking devices have been used to couple a graft to tissue during hernia procedures. Generally, the tacking devices comprise one or more surfaces intended to engage or pierce through the graft and tissue to hold them in close contact. While tacking devices may be less time consuming than suturing, many tacking devices are still difficult to deploy and, if not deployed at a proper location, may cause surgical complications.

SUMMARY

The present embodiments systems and methods for repairing tissue using one or more tacking devices. In one embodiment, the system comprises a graft member and at least one protective member configured to enclose at least a portion of a tacking device. The protective member may include, without limitation, a pocket having an enclosure forming an interior space, a plug of material or a barrier layer. When at least one tacking device is deployed to couple the graft member to the tissue, at least a portion of the tacking device is enclosed by the protective member to reduce the exposure of the tacking device.

Advantageously, the one or more protective members may reduce the exposure of portions of the tacking device. For example, when the graft member is used to treat a ventral abdominal hernia, the protective members may reduce or eliminate exposure of the tacking device into the peritoneum, which may reduce the risk of complications such as inadvertent snagging on the intestines.

The protective members may comprise various shapes and sizes. For example, in one embodiment, the protective members comprise multiple discrete pockets coupled to the graft member and spaced apart along a perimeter of the graft member. The pockets may comprise a dome-shaped enclosure, longitudinal strips, or other configurations.

The one or more tacking devices may be delivered within a hollow lumen of an insertion tool in a delivery state, and may be deployed using multiple techniques. For example, a laparoscopic delivery technique may be used in which the insertion tool is advanced through a laparoscopic device and through the pocket prior to piercing the graft member. Alternatively, a percutaneous delivery technique may be used in which the insertion tool is advanced directly through abdominal skin, but preferably does not pierce through the pocket. As a further alternative, an endoscopic or open technique may be used. In any of the above techniques, multiple tacking devices may be loaded in a sequential manner within the hollow lumen of the insertion tool, and then sequentially deployed to secure the graft member to the tissue at multiple different locations.

In an alternative embodiment, the protective member may comprise at least one barrier layer disposed distal to the second surface of the graft member. The insertion tool may comprise a sharpened tip configured to pierce through the tissue and at least a portion of the graft member, but not pierce through the barrier layer when the tacking devices are delivered percutaneously. When the insertion tool contacts the barrier layer, a physician may know when to cease advancement of the insertion tool and then may deploy the tacking devices.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

In the present application, the term "proximal" refers to a direction that is generally towards a physician during a medical procedure, while the term "distal" refers to a direction that is generally towards a target site within a patent's anatomy during a medical procedure. Thus, "proximal" and "distal" portions of a device or bodily region may depend on the point of entry for the procedure (e.g., percutaneously versus laparoscopically).

Figure 1:
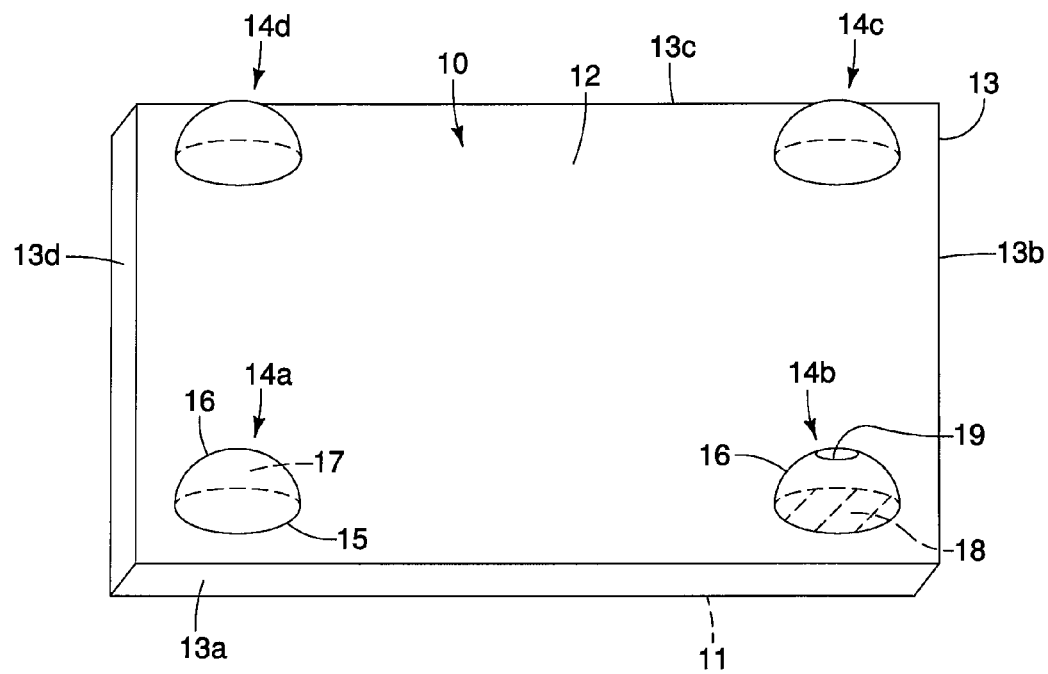
FIG. 1 is a perspective view of a graft member and multiple discrete pockets.

Referring now to FIG. 1, a first embodiment of a graft member and at least one protective member are shown. In this embodiment, the protective members are in the form of pockets for receiving at least one tacking device. As will be explained further below, the protective member need not form a pocket but may, for example, comprise a plug of material or barrier layer coupled within or adjacent to the graft member.

The graft member 10 has a first surface 11 and a second surface 12. If used to treat a ventral abdominal hernia, as explained below, the first surface 11 may be disposed adjacent to abdominal tissue 74, while the second surface 12 may face towards the peritoneum. In the example of FIG. 1, the graft member 10 comprises a generally rectangular shape having a four-sided perimeter 13 defined by sides 13a-13d. However, the graft member 10 may comprise other shapes, such as the elliptical shape shown in FIG. 14, or any other suitable shape for covering tissue.

In the embodiment of FIG. 1, multiple protective members are provided in the form of four pockets 14a-14d that are coupled to the graft member 10 for receiving a tacking device or other member used to attach the graft member 10 to the tissue 74. In this example, each of the four pockets 14a-14d comprises a generally dome-shaped configuration including a rim 15, an enclosure 16, and an interior region 17. However, as will be explained further below, the pockets may comprise alternative shapes, including single rectangular or elliptical-shaped pockets, a plurality of longitudinal strips, and the like.

The pockets 14a-14d in FIG. 1 are positioned near the four corners of the rectangular-shaped graft member 10, and are disposed on the second surface 12 of the graft member 10. The rim 15 of each pocket 14a-14d may be coupled to the second surface 12 of the graft member 10 using any suitable technique, including but not limited to a biocompatible adhesive, heat bonding, or mechanical attachment devices.

The pockets 14a-14d may be formed of a material ranging in rigidity based on a desired application. For example, if a laparoscopic delivery approach is used, as explained in FIGS. 5-7 below, the pockets 14a-14d may comprise a material that may be punctured by a sharpened tip 52 of an insertion tool 50, as shown below. By contrast, if a percutaneous delivery approach is used, as explained in FIGS. 8-10 below, the pockets 14a-14d may comprise a material that cannot be punctured by the insertion tool 50, thereby reducing or eliminating the possibility of advancing the sharpened tip 52 of the insertion tool 50 into the peritoneum. Solely by way of example, and without limitation, the pockets 14a-14d may be formed from silicone, urethanes, metal, plastic, rigid polyethylene, collagenous materials (cross-linked or otherwise), biopolymers, or any other suitable material.

Further, the pockets 14a-14d may comprise resorbable polymers in instances where only temporary pocket protection is needed, e.g., where the tacking device also is resorbable, or when snagging of a tacking device is a concern only during deployment or shortly thereafter. However, permanent or significantly prolonged protection of the pockets 14a-14d may be provided, depending on the nature of a procedure.

Figure 2:
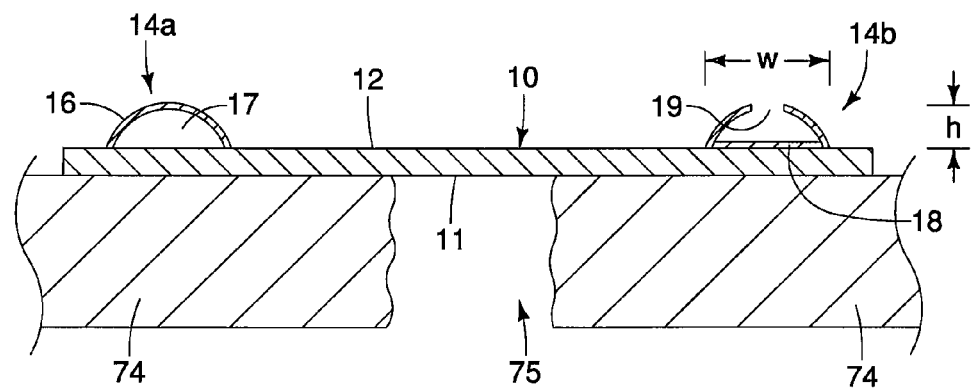
FIG. 2 is a side-sectional view illustrating the graft member of FIG. 1 adjacent to tissue having a ventral hernia.

Optionally, one or more pockets 14a-14d may comprise a base member 18 disposed adjacent to the second surface 12 of the graft member 10. In FIGS. 1-2, the pocket 14b comprises a disc-shaped base member 18 formed within the rim 15. If used, the base member 18 may comprise a semi-rigid material that is penetrable by a tacking device and/or an insertion tool, with a predetermined level of resistance to provide tactile feedback to a physician. As a further option, the interior space 17 of one or more pockets 14a-14d may be filled with a penetrable substance, such as silicone, to provide tactile feedback to a physician during positioning and delivery of tacking devices, as explained further below.

The graft member 10 may comprise any suitable material for covering a perforation, and substantially or entirely inhibiting the protrusion of abdominal matter. In one embodiment, the graft member 10 may comprise porcine small intestinal submucosa (SIS), such as SURGISIS® BIODESIGN™ Soft Tissue Graft, available from Cook Medical, Inc., Bloomington, Ind., which provides smart or "site-appropriate" tissue remodeling through its three-dimensional extracellular matrix (ECM) that is colonized by host tissue cells and blood vessels, and provides a scaffold for connective and epithelial tissue growth and differentiation along with the ECM components. The graft member 10 would be a one to four layer lyophilized soft tissue graft made from any number of tissue engineered products. Reconstituted or naturally-derived collagenous materials can be used, and such materials that are at least bioresorbable will provide an advantage, with materials that are bioremodelable and promote cellular invasion and ingrowth providing particular advantage. Suitable bioremodelable materials can be provided by collagenous ECMs possessing biotropic properties, including in certain forms angiogenic collagenous extracellular matrix materials. For example, suitable collagenous materials include ECMs such as submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa, including small intestinal submucosa, stomach submucosa, urinary bladder submucosa, and uterine submucosa. The graft member 10 may also comprise a composite of a biomaterial and a biodegradable polymer. Additional details may be found in U.S. Pat. No. 6,206,931 to Cook et al., the disclosure of which is incorporated herein by reference in its entirety.

Referring now to FIG. 2, the graft member 10, having pockets 14a-14d coupled thereto, may be used to cover a perforation 75. In the example shown, the perforation 75 is a ventral hernia located in the tissue 74 of the abdominal wall. While treatment of a ventral hernia is shown for illustrative purposes, it will be apparent that the graft member and protective members described herein may be used in a wide range of medical procedures, including but not limited to any exemplary procedures described herein. As will be explained in greater detail below, one or more tacking devices may be deployed at least partially within one or more of the pockets 14a-14d, and the pockets 14a-14d may reduce or eliminate the risk of complications such as inadvertent snagging of the tacking devices on organs such as the intestines.

Figure 7:
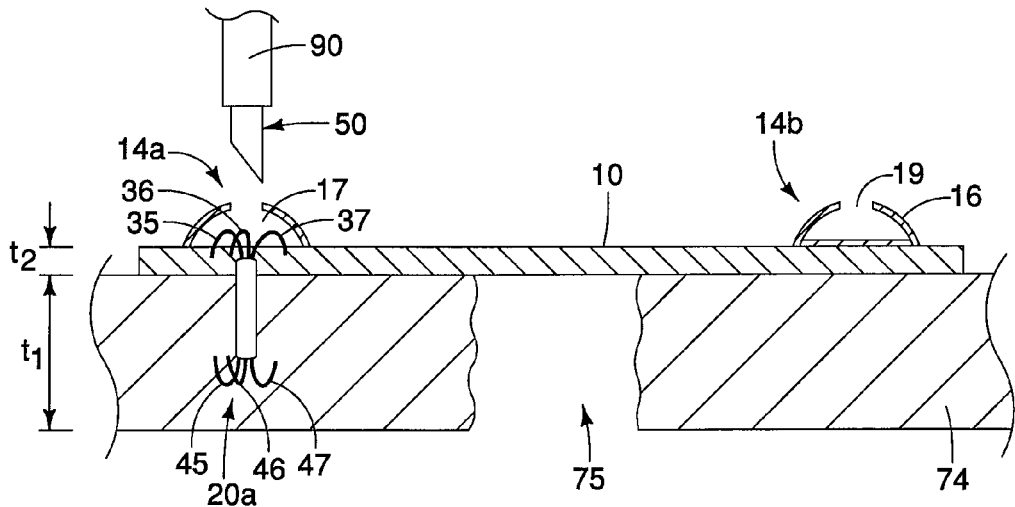
Figure 9:
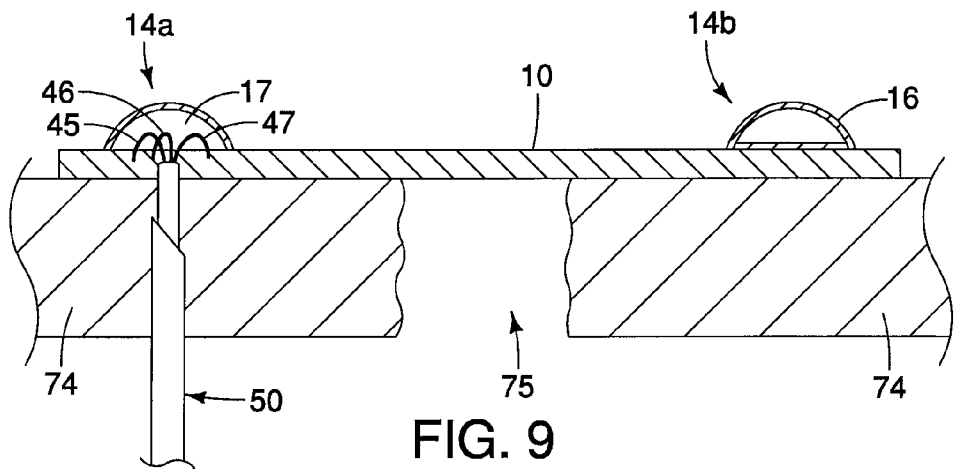
Figure 10:
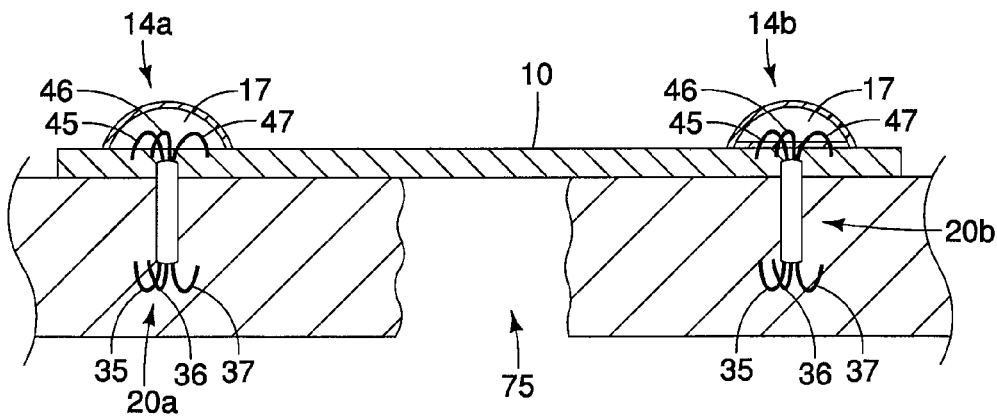

By way of example, in the embodiment of FIGS. 1-2, the pockets 14a-14d each may comprise a height h and a width w, which yields a volume within the interior space 17. The volume within the interior space 17 is greater than the portion of the tacking device disposed therein, and thereby permitting deployment of a distal portion of the tacking device within the interior space 17, as depicted in FIGS. 7, 9 and 10 below. In one embodiment, the interior space 17 comprises at least 30% open space when the tacking device is fully deployed, i.e., the open space is not fully occupied by the tacking device. The provision of additional open space within the enclosure 16 may facilitate deployment of the tacking device therein, and the enclosure 16 may otherwise not interfere with the tacking device.

In the embodiment of FIGS. 1-2, the pocket 14b comprises a pre-formed bore 19 formed through a surface of the enclosure 16. The pre-formed bore 19 may be provided in any or all of the pockets 14a-14d, preferably when a laparoscopic or endoscopic approach is used, since in these techniques the insertion tool 50 will be advanced in a direction from the peritoneum through the enclosure 16 and through the graft member 10. The pre-formed bore 19 may provide a physician with a guide through which the insertion tool 50 should be advanced in the laparoscopic and endoscopic approaches. However, the pre-formed bore 19 may be omitted and the enclosures 16 of the pockets 14a-14d may simply comprise penetrable layers that may be pierced by the insertion tool.

Figure 3:
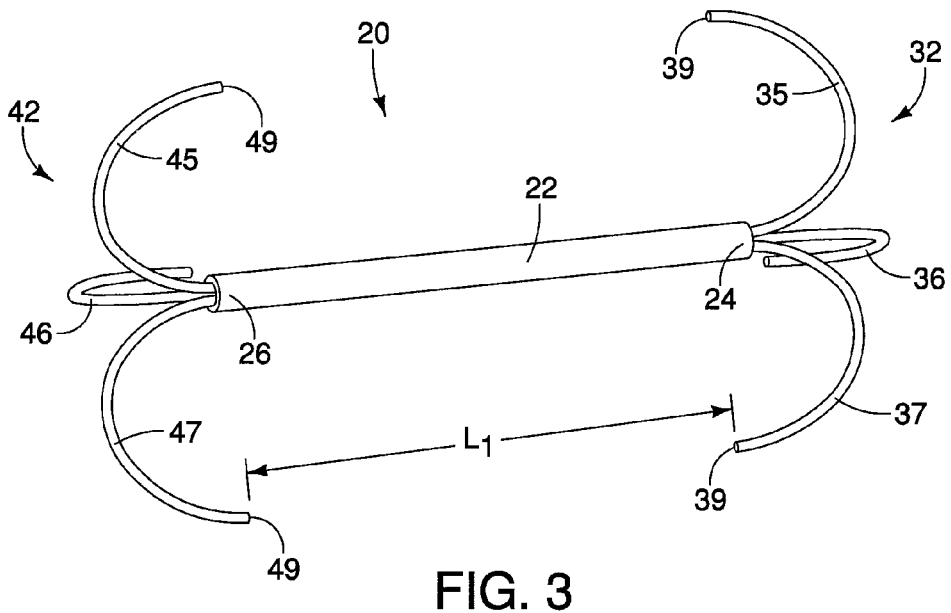
FIG. 3 is a perspective view of an exemplary tacking device.

Referring now to FIG. 3, a first embodiment of a tacking device 20, which may be used in conjunction with the graft member 10 and the pockets 14a-14d, is described. The illustrated tacking device 20 is described in further detail in U.S. application Ser. No. 12/428,226, filed Apr. 22, 2009 (hereinafter "the '226 application"), which is hereby incorporated by reference in its entirety. It will be noted that the tacking device 20 of the '226 application is merely one example of a tacking device that may couple a graft member to tissue, and which may be used with the graft member 10 and pockets 14a-14d, but many other tacking device configurations are possible including helical, rigid, semi-rigid, expandable, or those that maintain a constant shape.

As described in detail in the '226 application, the tacking device 20 may comprise at least one tube member 22 having a proximal end 24 and a distal end 26. The tacking device 20 further comprises a proximal deployment mechanism 32 and a distal deployment mechanism 42. In the embodiment of FIG. 3, the proximal deployment mechanism 32 comprises three proximal deployable members 35-37, while the distal deployment mechanism 42 comprises three distal deployable members 45-47. The proximal deployable members 35-37 extend proximally from the proximal end 24 of the tube member 22, while the distal deployable members 45-47 extend distally from the distal end 26 of the tube member 22, as shown in FIG. 3. In the embodiment of FIG. 3, since the device is symmetrical, it may be loaded into an insertion tool with either end first.

The proximal deployable members 35-37 and the distal deployable members 45-47 each may be affixed relative to the tube member 22. In one embodiment, each of the proximal and distal deployable members 35-37 and 45-47 may be separate and discrete elements. Accordingly, six separate deployable members may be provided. Specifically, the three proximal deployable members 35-37 may be coupled to the tube member 22 near the proximal end 24 of the tube member 22. The three proximal deployable members 35-37 may be coupled to the proximal end 24 of the tube member 22 using an adhesive, frictional fit, mechanical device or other suitable mechanism or processes. Similarly, the three distal deployable members 45-47 may be coupled to the distal end 26 of the tube member 22 using an adhesive, frictional fit, mechanical device or other suitable mechanism. In an alternative embodiment, instead of providing six discrete deployable members, three wires may be disposed through the entirety of tube member 22, as explained further in the '226 application.

Figure 4:
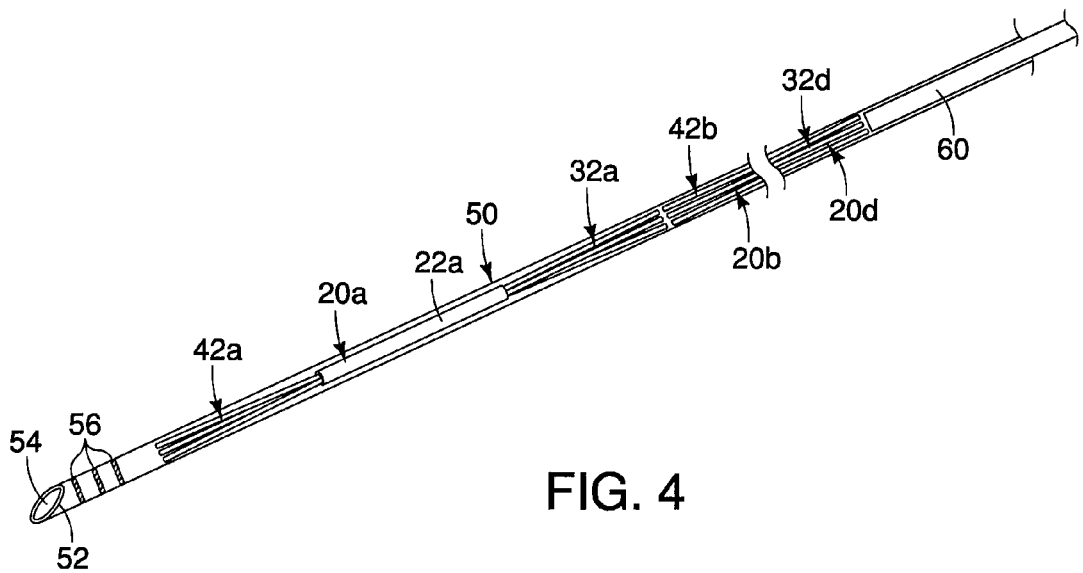
FIG. 4 is a perspective, cut-away view illustrating multiple tacking devices in a delivery configuration.

The proximal and distal deployable members 35-37 and 45-47 each comprise an expanded deployed configuration, as shown in FIG. 3, and further comprise a contracted delivery configuration, as shown in FIG. 4. In one embodiment, each of the deployable members 35-37 and 45-47 may comprise a hook-shaped configuration in the expanded state. For example, the deployable members 35-37 and 45-47 may comprise a curvature of about 90 to about 360 degrees in the expanded state, and more preferably about 180 degrees, as shown in FIG. 3. Where the deployable members 35-37 and 45-47 "retroflex" and comprises a curvature of about 180 degrees, the end regions 39 and 49 of the proximal and distal deployable members are oriented substantially parallel to the tube member 22. Moreover, the end regions 39 and 49 may be radially spaced apart from one another in the expanded state, as shown in FIG. 3. In this configuration, the end regions 39 and 49 may be well-suited for engaging, grasping, piercing and/or abutting tissue or graft material.

Further, a longitudinal distance $L_1$ between the end regions 39 and 49 of the tacking device 20 may be varied to engage tissue in a desirable manner. For example, the longitudinal distance $L_1$ may be dimensioned to be substantially equal to or less than the combined thickness $t_1$ and $t_2$ of a tissue 74 and a graft member 10, respectively, as shown in FIG. 7 below, thereby providing a desired compressive force upon the tissue 74 and the graft member 10. As explained further in the '226 application, the dimensions of the tacking device 20 may be tailored based on a particular surgical procedure, a particular patient's anatomy and/or other factors.

The deployable members 35-37 and 45-47 may comprise a shape-memory material, such as a nickel-titanium alloy (nitinol). If a shape-memory material such as nitinol is employed, the deployable members 35-37 and 45-47 may be manufactured such that they can assume the preconfigured expanded state shown in FIG. 3 upon application of a certain cold or hot medium. More specifically, a shape-memory material may undergo a substantially reversible phase transformation that allows it to "remember" and return to a previous shape or configuration. For example, in the case of nitinol, a transformation between an austenitic phase and a martensitic phase may occur by cooling and/or heating (shape memory effect) or by isothermally applying and/or removing stress (superelastic effect). Austenite is characteristically the stronger phase and martensite is the more easily deformable phase.

In an example of the shape-memory effect, a nickel-titanium alloy having an initial configuration in the austenitic phase may be cooled below a transformation temperature $(M_f)$ to the martensitic phase and then deformed to a second configuration. Upon heating to another transformation temperature $(A_f)$, the material may spontaneously return to its initial, predetermined configuration, as shown in FIG. 3. Generally, the memory effect is one-way, which means that the spontaneous change from one configuration to another occurs only upon heating. However, it is possible to obtain a two-way shape memory effect, in which a shape memory material spontaneously changes shape upon cooling as well as upon heating.

Alternatively, the deployable members 35-37 and 45-47 may be made from other metals and alloys that are biased, such that they may be restrained by the insertion tool 50 prior to deployment, but are inclined to return to their relaxed, expanded configuration upon deployment. Solely by way of example, the deployable members 35-37 and 45-47 may comprise other materials such as stainless steel, cobalt-chrome alloys, amorphous metals, tantalum, platinum, gold and titanium. The deployable members 35-37 and 45-47 also may be made from non-metallic materials, such as thermoplastics and other polymers. As noted above, the deployable members 35-37 and 45-47 may comprise any shape suitable for engaging, penetrating and/or abutting tissue, for purposes explained further below, and need not necessarily assume the curved shape depicted in FIG. 3.

Referring to FIG. 4, one or more tacking devices 20 may be delivered to a target site in a patient's anatomy using an insertion tool 50. In one embodiment, the insertion tool 50 is capable of carrying multiple different tacking devices, such as four tacking devices 20a-20d, as depicted in FIG. 4 and explained further in the '226 application.

In one embodiment, the insertion tool 50 comprises a needle-like body having a sharpened distal tip 52 and a hollow lumen 54, as shown in FIG. 4. The insertion tool 50 may be manufactured from stainless steel or any other suitable material, and may comprise an endoscopic ultrasound (EUS), or echogenic, needle. Solely by way of example, the insertion tool 50 may comprise the EchoTip® Ultrasound Needle, or the EchoTip® Ultra Endoscopic Ultrasound Needle, both manufactured by Cook Endoscopy of Winston-Salem, N.C.

The hollow lumen 54 of the insertion tool 50 may comprise an inner diameter that is larger than an outer diameter of the tacking device 20. Therefore, one or more tacking devices may be loaded into the hollow lumen 54 in a delivery configuration, as shown in FIG. 4. In the delivery configuration, the proximal and distal deployable members 35-37 and 45-47 of each tacking device 20a-20f may comprise a substantially longitudinally-oriented profile, i.e., oriented along a longitudinal axis of the insertion tool 50. The multiple tacking devices 20a-20f may be inserted into the hollow lumen 54 of the insertion tool 50 in a sequential manner, whereby the proximal deployment mechanism 32a of the first tacking device 20a may abut the distal deployment mechanism 42b of the second tacking device 20b, as depicted in FIG. 4.

A stylet 60 may be disposed for longitudinal movement within the hollow lumen 52 of the insertion tool 50, as shown in FIG. 4. The stylet 60 is disposed proximal to the proximal deployment mechanism 32d of the final sequential tacking device 20d. During use, the insertion tool 50 may be proximally retracted, while the stylet 60 may be held longitudinally steady, to facilitate sequential deployment of each of the tacking devices 20a-20d, as explained further below.

The insertion tool 50 may comprise one or more markers 56, as shown in FIG. 4, which may be disposed near the distal end of the insertion tool 50. The markers 56 may be configured to be visualized under fluoroscopy of other imaging techniques to facilitate location of the distal end of the insertion tool, for example, so that a physician may determine how far the insertion tool 50 has penetrated into tissue 74, the graft member 10 and/or the pockets 14a-14d, as depicted in FIGS. 5-6 and 8-9 below.

Figure 5:
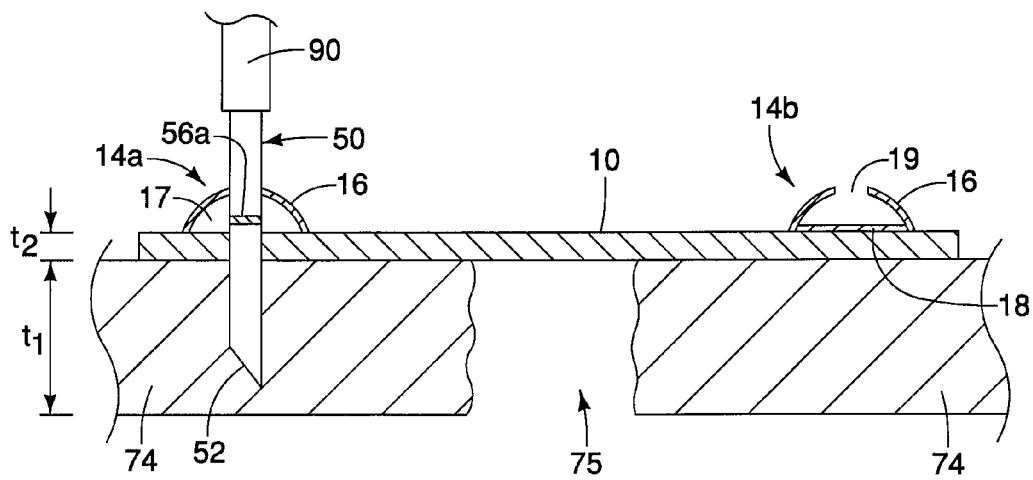
FIGS. 5-7 are side-sectional views illustrating an exemplary laparoscopic deployment of one or more of the tacking devices of FIGS. 3-4 to treat a ventral hernia.
Figure 6:
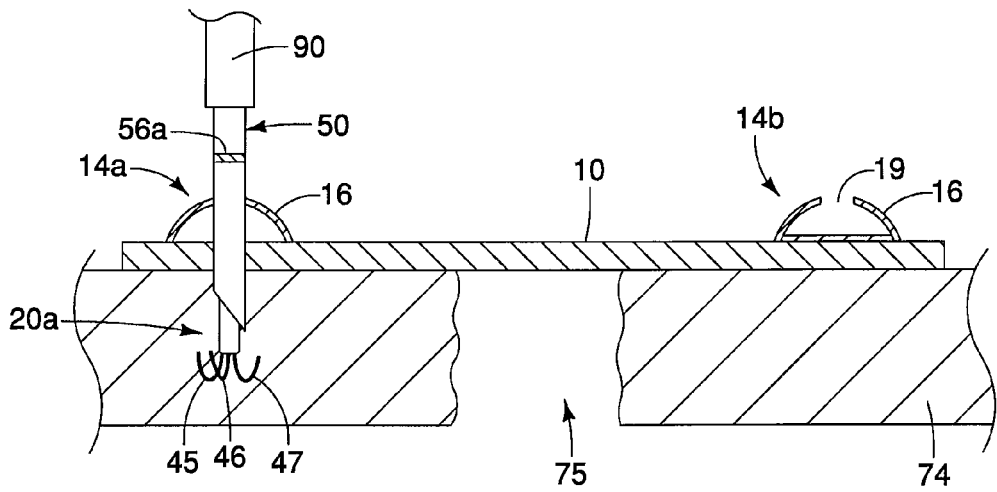

Referring now to FIGS. 5-7, one or more tacking devices 20 described above may be used with the graft member 10 and the pockets 14a-14d to facilitate treatment of the perforation 75 in the tissue 74 of the abdominal wall. In the example of FIGS. 5-7, a laparoscopic technique is employed whereby multiple relatively small incisions are made to access the hernia site. A first laparoscopic device (not shown) may be used to visualize the peritoneum, while a second laparoscopic device 90 may be used to deliver the insertion tool 50.

The initial stages of the ventral hernia repair may be performed using techniques that are known. In one exemplary technique, multiple sutures (not shown) may be tied to the graft member 10, preferably along the perimeter 13 defined by the four sides 13a-13d of the graft member 10. The graft member 10 may be rolled up and inserted into the peritoneum using known methods. Once in the peritoneum, a physician may use the first laparoscopic device to visualize the graft member 10, and the graft member 10 then is unrolled. Alternatively, another suitable visualization device, in lieu of a laparoscope, may be used. Subsequently, one or more needles may be percutaneously advanced towards the peritoneum, and one or more grasping devices may be advanced through the needles. The grasping devices may grasp the multiple sutures attached to the graft member 10. The sutures then may be tensioned to pull the unrolled graft member 10 in a direction towards the tissue 74 to hold the graft member 10 in place during the procedure.

Referring now to FIG. 5, after the graft member 10 has been placed to cover the perforation 75, a laparoscopic device 90 may be maneuvered into a desired position within the peritoneum. The distal end of the laparoscopic device 90 may be positioned facing the graft member 10, as shown in FIG. 5. In a next step, the insertion tool 50 may be advanced distally through a lumen of the laparoscopic device 90 to pierce through the enclosure 16 of the first pocket 14a and into the interior region 17 of the first pocket 14a. As noted above, any of the enclosures 16 may comprise the pre-formed bore 19, which may be about the diameter of the insertion tool 50, and which may be used as a pre-formed guide for the insertion tool 50.

The insertion tool 50 then is further advanced to pierce through the graft member 10, and further may pierce at least partially into the tissue 74 at a first location around the perimeter of the perforation 75, as depicted in FIG. 5. A physician may identify the location of the pockets 14a-14d using a laparoscope or an endoscope placed in the peritoneum, or another suitable visualization device.

In this example, the insertion tool 50 is carrying four sequential tacking devices 20a-20d, which may be disposed within the hollow lumen 54 of the insertion tool 50 as explained in FIG. 4 above. With the tacking devices 20a-20d in the contracted delivery states, the sharpened tip 52 of the insertion tool 50 may be advanced to a predetermined depth into the tissue 74. The markers 56 of FIG. 4 may facilitate in determining how far the insertion tool 50 has penetrated into the tissue 74. Moreover, if the penetrable base member 18 is provided, or if a substance such as silicone is disposed within the interior space 17 as noted above, either may provide a physician with tactile feedback to facilitate the positioning of the insertion tool 50.

In a next step, the stylet 60 of FIG. 4 may be held steady with respect to the insertion tool 50, while the insertion tool 50 is retracted in a proximal direction, i.e., away from the tissue 74 and towards the peritoneum. This causes the distal deployable members 45-47 of the most distal tacking device 20a to extend distal to the sharpened tip 52 of the insertion tool 50, as depicted in FIG. 6. When the distal deployable members 45-47 are no longer radially constrained by the insertion tool 50, they may assume their predetermined expanded configurations in which they may engage, penetrate and/or abut the tissue 74. As the insertion tool 50 further is retracted proximally with respect to the tacking device 20*a*, the proximal deployable members 35-37 may assume their predetermined expanded configuration when are no longer radially constrained, as shown in FIG. 7.

Notably, when using the laparoscopic technique of FIGS. 5-7, a physician may position the distal deployable members 45-47 at a predetermined distance within the tissue 74, preferably with the assistance of the markers 56, to ensure that the proximal deployable members 35-37 will be deployed at the correct location within the pockets 14*a*-14*d*, and to engage the graft member 10, upon exiting the insertion tool 50. Preferably, at least one specific marker 56*a* may be used to identify the location of the proximal deployable members 35-37 within the insertion tool 50. Accordingly, when the marker 56*a* is positioned in or near the interior space 17 of the pocket 14*a*, as shown in FIG. 5, a physician may know to begin the deployment of the tacking device 20 to land the proximal deployable members 35-37 within the interior space 17.

In the expanded configuration, the proximal deployable members 35-37 may engage, penetrate and/or abut the graft member 10 and optionally penetrate into the tissue 74. In this manner, the tacking device 20*a* helps secure the graft material 10 against the tissue 74. In particular, the substantially 180-degree hook-shaped configuration of the proximal deployable members 35-37 may urge the graft member 10 in a distal direction towards the tissue 74.

After the first tacking device 20*a* has been deployed, the insertion tool 50 may be repositioned to deploy another tacking device around the perimeter of the perforation 75. Each subsequent tacking device 20*b*-20*d* may be deployed in the same manner as the tacking device 20*a*. In this manner, the tacking devices 20*a*-20*d* may secure the graft member 10 around the perimeter of the perforation 75. As will be apparent, greater or fewer tacking devices may be used, and the positioning of the tacking devices may be varied to optimize securing the graft member 10 to the tissue 74 in order to substantially seal the perforation 75.

Advantageously, the pockets 14*a*-14*d* substantially reduce or eliminate the exposure of any portion of the tacking devices 20*a*-20*d* within the peritoneum when coupling the graft member 10 to the abdominal tissue 74. Since the exposure of the tacking device 20 into the peritoneum may be reduced or eliminated, it reduces the risk of complications such as inadvertent snagging of the tacking device on the intestines.

Figure 8:
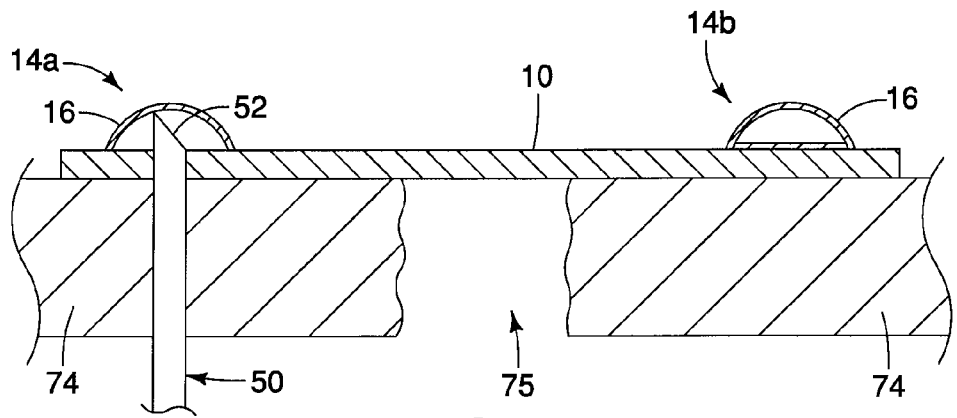
FIGS. 8-10 are side-sectional views illustrating an exemplary percutaneous deployment of one or more of the tacking devices of FIGS. 3-4 to treat a ventral hernia.

Referring now to FIGS. 8-10, a percutaneous approach for treatment of a ventral hernia is described. The percutaneous approach is similar to the laparoscopic approach described in FIGS. 5-7 above, but with some notable differences. First, in the percutaneous technique, then insertion tool 50 is advanced in a direction from the abdominal tissue 74 towards the graft member 10. Further, the insertion tool 50 may be advanced directly through a patient's abdominal skin.

In the percutaneous approach, the insertion tool 50 is advanced directly through a patient's abdominal skin, through the tissue 74, and may be advanced just distal to the graft member 10 and at least partially into the first pocket 14*a*, as shown in FIG. 8. The sharpened tip 52 of the insertion tool 50 may contact the enclosure 16 of the first pocket 14*a*, thereby indicating to a physician that the sharpened tip 52 is within the interior space 17 of the first pocket 14*a*, as depicted in FIG. 8. In order to optimally visualize the insertion tool 50, a laparoscopic viewing device may be positioned in the peritoneum, or an endoscope may be translumenally advanced in proximity to the pockets 14*a*-14*d*. Alternatively, the insertion tool 50, and markers 56 in particular, may be viewed using fluoroscopy or other suitable techniques.

In a next step, the stylet 60 of FIG. 4 may be held steady with respect to the insertion tool 50, while the insertion tool 50 is retracted in a proximal direction, i.e., away from the peritoneum and towards the tissue 74. This causes the distal deployable members 45-47 of the most distal tacking device 20*a* to extend distal to the sharpened tip 52 of the insertion tool 50, as depicted in FIG. 9. When the distal deployable members 45-47 are no longer radially constrained by the insertion tool 50, they may assume their predetermined expanded configurations in which they may engage, penetrate and/or abut the graft member 10 and optionally penetrate into the tissue 74. As the insertion tool 50 further is retracted proximally with respect to the tacking device 20*a*, the proximal deployable members 35-37 may assume their predetermined expanded configuration when are no longer radially constrained, as shown in FIG. 10. In the expanded configuration, the proximal deployable members 35-37 may engage, penetrate and/or abut the tissue 74. In this manner, the tacking device 20*a* helps secure the graft material 10 against the tissue 74, and in particular, the substantially 180-degree hook-shaped configuration of the distal deployable members 45-47 may urge the graft member 10 in a direction towards the tissue 74.

Notably, in the percutaneous approach of FIGS. 8-10, the distal deployable members 45-47 engage the graft member 10, as opposed to the laparoscopic approach of FIGS. 5-7 where the proximal deployable members 35-57 engage the graft member 10, since the insertion tool 50 enters and deploys the tacking device 20 in opposite directions. Further, as generally described above, after the first tacking device 20*a* has been deployed, the insertion tool 50 may be repositioned to deploy additional tacking devices around the perimeter of the perforation 75.

In the percutaneous approach of FIGS. 8-10, the pre-formed pocket bores 19 are omitted to reduce or eliminate the likelihood of the insertion tool 50 being advanced into the peritoneum. Rather, with a percutaneous approach, the enclosure 16 of the pockets 14*a*-14*d* may comprise a solid and relatively rigid material or have a barrier that is impenetrable by the insertion tool 50. Accordingly, when the insertion tool 50 contacts the enclosure 16, a physician may know when to cease advancement of the insertion tool 50.

In a further alternative technique, an endoscopic approach for treatment of a ventral hernia may be used. The endoscopic approach is similar to the laparoscopic approach described in FIGS. 5-7 above, however, an endoscope is used instead of the laparoscopic device 90, and no visible incisions may be made on the skin of the patient. In particular, the endoscope may be advanced through a bodily lumen such as the alimentary canal, with an access hole being created through the alimentary canal, to obtain peritoneal access to the ventral hernia. One or more components, such as the insertion tool 50, then may be advanced through a working lumen of the endoscope. The distal end of the insertion tool 50 may be viewed via optical elements of the endoscope. Under suitable visualization using a light source and an eyepiece, a physician may deploy multiple tacking devices one at one time using the insertion tool 50. If this endoscopic approach is employed, the insertion tool 50 may carry additional tacking devices 20 to subsequently close the access hole in the alimentary canal.

Figure 11:
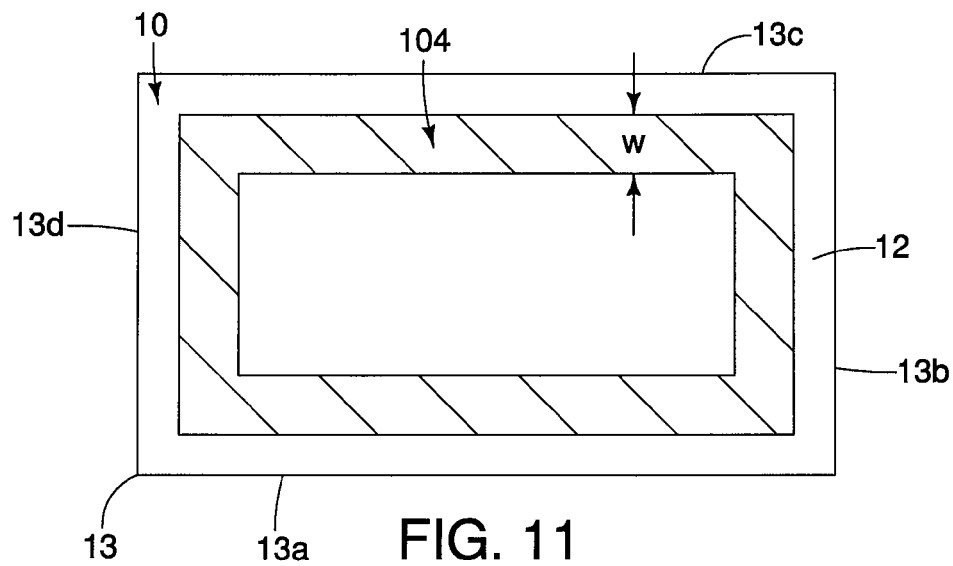
FIGS. 11-12 are, respectively, top and side views of an alternative embodiment of a pocket.
Figure 12:
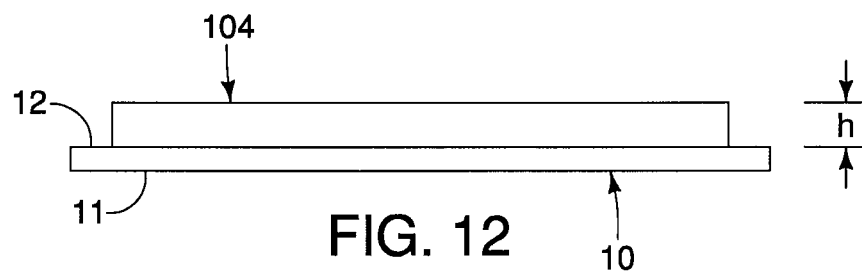

Referring now to FIGS. 11-14, exemplary variations of the protective members are shown. In FIGS. 11-12, a single pocket 104 is disposed along the perimeter 13 of the second surface 12 of the graft material 10, preferably at a distance inward from the perimeter 13 defined by the four sides 13*a*-13*d*. The pocket 104 may comprise a height h and a width w, which like the pockets 14*a*-14*d* above are sized to receive at least a portion of a tacking device. In the embodiment of FIGS. 11-12, multiple tacking devices may be sequentially deployed at spaced apart locations within the single pocket 104.

Figure 13:
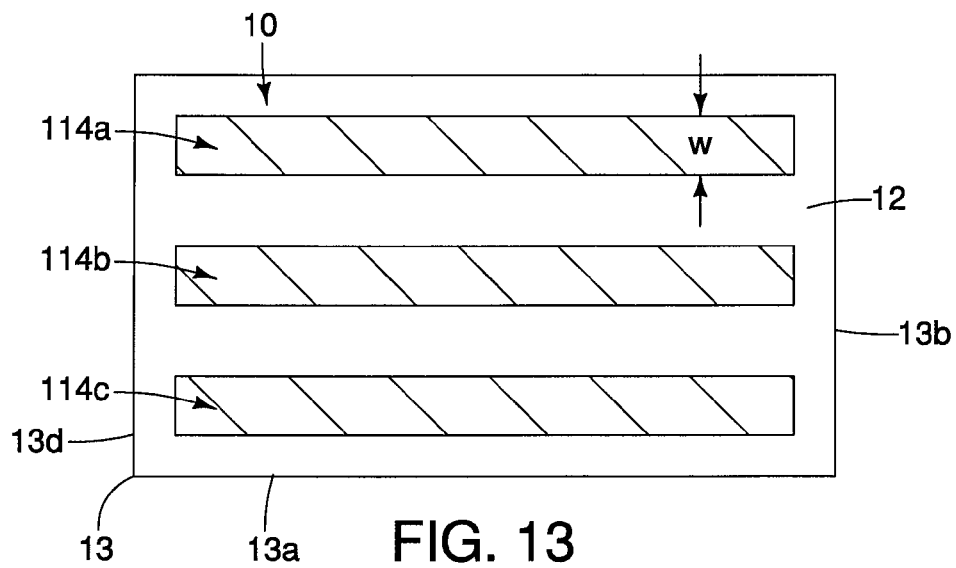
FIG. 13 is a top view of a further alternative embodiment having a series of pockets.
Figure 14:
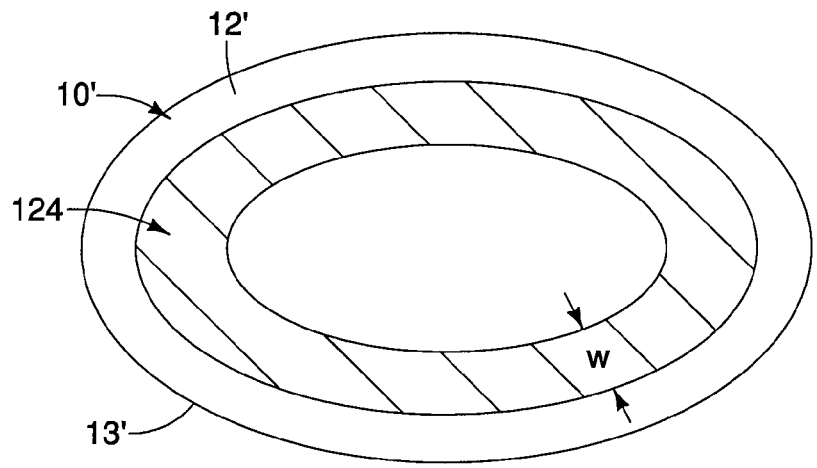
FIG. 14 is a top view of a further alternative embodiment of a graft member and pocket.

In FIG. 13, multiple pockets 114a-114c are provided in the form of longitudinal strips having a height and a width sized to receive at least a portion of one or more tacking devices, in the manner described above. In FIG. 14, an alternative graft member 10' comprises an elliptical shape, and a single pocket 124 comprises an elliptical shape disposed on the second surface 12' of the graft material 10' and preferably inward from the perimeter 13'.

In the embodiments of FIGS. 1 and 11-14, as an alternative to a pocket having an enclosure forming an interior space, the protective members may comprise plugs of material that enclose portions of the deployed tacking device 20. For example, in lieu of a dome-shaped enclosure 16, the protective member may comprise a dome-shaped plug adhered to the second surface 12 of the graft member 10, or in lieu of the pockets having longitudinal strips 114a-114c, longitudinal plugs of material may be disposed on the second surface 12 of the graft member 10. The longitudinal plugs may be formed of silicone or another suitable material configured to perform substantially the same functions as the pockets described in FIGS. 1 and 11-14, and in particular, to enclose and protect at least a portion of the tacking device.

Figure 15:
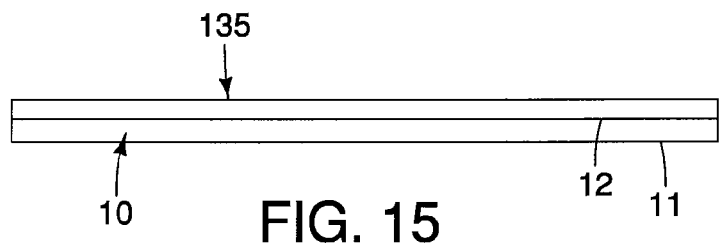
FIG. 15 is a side view of an alternative embodiment having a barrier layer adjacent to a graft member.

Referring now to FIG. 15, an alternative system suitable for use with the percutaneous delivery approach of FIGS. 8-10 is described. In FIG. 15, the protective member comprises at least one barrier layer 135 disposed distal to the second surface 12 of the graft member 10. In the percutaneous delivery explained above, the insertion tool 50 comprises a sharpened tip 52 configured to pierce through the tissue 74 and at least a portion of the graft member 10. However, in the example of FIG. 15, the sharpened tip 52 cannot pierce through the barrier layer 135. The barrier layer 135 may comprise a material that is substantially or entirely impenetrable by the insertion tool 50, but the material still permits the barrier layer 135 to be rolled up during delivery of the graft member 10. Solely by way of example, the barrier layer 135 may comprise relatively thin and rigid polyethylene, or any other biocompatible material. Moreover, the barrier layer 135 may comprises a single sheet of material that substantially covers the entire second surface 12 of the graft member 10, as depicted in FIG. 15.

In this example, a physician may percutaneously advance the insertion tool 50 distally towards the peritoneum, and once resistance is encountered by the sharpened tip 52 of the insertion tool 50 contacting the barrier layer 135, a physician then may know that the insertion tool 50 is at a depth suitable to initiate the deployment sequence of the tacking devices, as explained in FIGS. 8-10 above. Furthermore, one or more barrier layers 135 may be used with the pockets 14a-14d, 104, 114a-114c or 124 described above, in which case the barrier layer 135 may be disposed distal to the enclosure 16 of the at least one pocket 14a-14d, 104, 114a-114c or 124 to reduce the likelihood of the insertion tool reaching the peritoneum.

Figure 16:
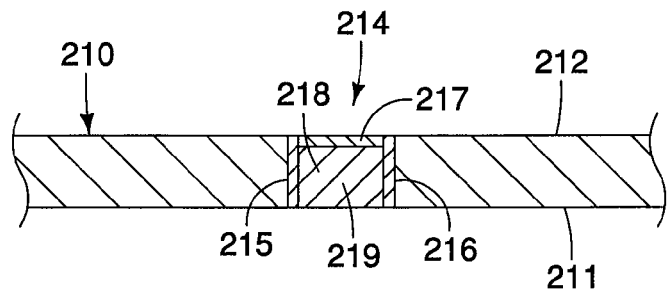
FIG. 16 is a side view of an alternative embodiment having a protective member formed substantially within a graft member.

Referring now to FIG. 16, in yet a further alternative embodiment, a protective member may be formed substantially within a graft member. In this example, alternative graft member 210 has first and second surfaces 211 and 212. Protective member 214 comprises first and second side walls 215 and 216, plus end wall 217. The three walls 215-217 form a partial rectangular shape having one side open, as depicted in FIG. 16, for receipt of a portion of a tacking device. An interior space 218, formed between the walls 215-217, may comprise graft material or a substance 219. The substance 219 may be penetrable by a tacking device and/or insertion tool, with a predetermined level of resistance to provide tactile feedback to a physician. In one example, the substance 219 comprises silicone, although other suitable materials may be used.

The first and second side walls 215 and 216 and end wall 217 may be formed of a rigid or semi-rigid material, and may be coupled to the graft member 210, for example, using sutures. The protective member 214 is formed within the graft member 210 substantially between the first and second surfaces 211 and 212.

In use, a physician may percutaneously advance the insertion tool 50 distally towards the peritoneum, through tissue, and between the first and second side walls 215 and 216 coupled to the graft member 210. Once resistance is encountered by the sharpened tip 52 of the insertion tool 50 contacting the end wall 217 of the protective member 214, a physician then may know that the insertion tool 50 is at a depth suitable to initiate the deployment sequence of the tacking devices, as explained in FIGS. 8-10 above. Upon deployment, at least a portion of the tacking device is disposed within the interior space 217 of the protective member 214, within which a section of the graft member or substance 219 is disposed, thereby securing the graft member 210 to tissue and partially enclosing the tacking device.

Alternatively, the rigid or semi-rigid walls 215-217 may be omitted, and the protective member 214 may encompass a solid plug of material such as silicone. In this embodiment, the solid plug of material may be disposed substantially within the graft member 210 between the first and second surfaces 211 and 212 and be penetrable, yet provide tactile feedback to a physician to ensure optimal placement of the tacking device.

While the exemplary embodiments herein have illustrated the use of graft members and protective members, in conjunction with one or more tacking devices 20, for covering a perforation 75 formed in the ventral abdominal wall, the graft members and protective members disclosed herein may be useful in many other procedures. Solely by way of example, one or more graft members and protective members may be used to treat perforations in a visceral wall, such as the stomach wall. Further, the graft members and protective members may be used in conjunction with tacking devices to secure a graft member to tissue for reconstructing local tissue, and the like. It will be apparent that still further applications of the graft member and protective member are possible. Finally, while exemplary laparoscopic, endoscopic and percutaneous delivery techniques have been described, it should be noted that graft members and protective members described herein may be deployed at a target site during an open medical procedure.

It will be recognized by those skilled in the art that, while the methods described above generally include placing the devices in tissue through an internal bodily lumen, it will be recognized that the systems, devices and methods may be used on any layer of material (e.g. fabrics, cloth, polymers, elastomers, plastics and rubber) that may or may not be associated with a human or animal body and a bodily lumen. For example, the systems, devices and methods can find use in laboratory and industrial settings for placing devices through one or more layers of material that may or may not find application to the human or animal body, and likewise closing holes or perforations in layers of material that are not bodily tissue. Some examples include sewing or stitching and related manufacturing, working with synthetic tissues, connecting or repairing polymeric sheets, animal studies, veterinary applications, and post-mortem activities.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

I claim:

1. A system for securing a graft member to tissue, the system comprising:
    at least one tacking device;
    a graft member having first and second surfaces; and
    at least one protective member coupled to the graft member and configured to enclose at least a portion of the at least one tacking device that secures the graft member to tissue,
    wherein the protective member comprises at least one pocket including an enclosure forming an interior space, wherein at least the portion of the at least one tacking device is configured to be disposed within the interior space of the enclosure in a deployed state, and
    wherein the at least one pocket comprises a dome-shaped enclosure and a rim of the enclosure is coupled to the second surface of the graft member.

2. The system of claim 1 wherein multiple discrete pockets are coupled to the second surface of the graft member.

3. The system of claim 2 wherein the multiple discrete pockets are spaced apart along a perimeter of the graft material.

4. The system of claim 1 wherein at least a portion of the interior space of the pocket is filled with a penetrable substance.

5. The system of claim 1 wherein at least one of the tacking devices comprises proximal and distal deployable members, wherein each of the proximal and distal deployable members comprise hook-shaped configurations in the deployed state, and wherein at least one of the proximal or distal deployable members is at least partially disposed within the interior space of the enclosure when the tacking device is in the deployed state.

6. The system of claim 1 wherein the interior space of the at least one pocket comprises a volume having at least 30% open space when the tacking device is in the deployed state.

7. A method for securing a graft member to tissue, the method comprising:
    providing a graft member having first and second surfaces;
    providing a protective member coupled to the graft member, the protective member comprising at least one pocket comprising a dome-shaped enclosure forming an interior space, wherein a rim of the enclosure is coupled to the second surface of the graft member;
    positioning the first surface of the graft member with respect to a selected region of the tissue; and
    deploying at least one tacking device to couple the graft member to the tissue, such that at least a portion of the tacking device is disposed within the interior space of the enclosure in a deployed state.

8. The method of claim 7 wherein a laparoscopic delivery technique is used in which an insertion tool carrying the at least one tacking device is advanced through a laparoscopic device, through the interior space of the pocket, through the graft member, and then at least partially pierces through the tissue prior to deployment of the at least one tacking device.

9. The method of claim 7 wherein an endoscopic delivery technique is used in which an insertion tool carrying the at least one tacking device is advanced through an endoscope, through the interior space of the pocket, and pierces through the graft member and then at least partially through the tissue prior to deployment of the at least one tacking device.

10. The method of claim 7 wherein a percutaneous delivery technique is used in which an insertion tool is advanced directly through abdominal skin and then towards the graft member prior to deployment of the at least one tacking device.

11. The method of claim 10 wherein a sharpened tip of the insertion tool is positioned within the interior space of the at least one pocket prior to deployment of the at least one tacking device, wherein the insertion tool does not pierce through the enclosure.

12. A system for securing a graft member to tissue, the system comprising:
    a graft member having first and second surfaces;
    at least one barrier layer disposed distal to the second surface of the graft member;
    at least one tacking device configured to couple the graft member to the tissue; and
    an insertion tool for delivering the at least one tacking device, wherein the insertion tool comprises a sharpened tip configured to percutaneously pierce through the tissue and at least a portion of the graft member, and wherein the barrier layer comprises an undeflecting material such that it is not pierced by the sharpened tip.

13. The system of claim 12 wherein the barrier layer comprises a single sheet of material that is adjacent to substantially the entire second surface of the graft member.

14. A medical device for repairing tissue using at least one tacking device, the medical device comprising:
    a graft member having first and second surfaces; and
    at least one protective member coupled to the graft member and configured to enclose at least a portion of a tacking device that secures the graft member to tissue,
    wherein the protective member comprises at least one pocket including an enclosure forming an interior space, wherein at least a portion of the tacking device is disposed within the interior space of the enclosure in a deployed state, and
    wherein the pocket is formed at least partially within the graft member between the first and second surfaces.

15. The medical device of claim 14 wherein the pocket comprises two side walls and one end wall.

* * * * *